United States Patent [19]

Appel et al.

[11] 4,193,990

[45] Mar. 18, 1980

[54] HETEROTYPIC CANINE PARVOVIRUS VACCINE

[75] Inventors: Max J. G. Appel; Leland E. Carmichael, both of Ithaca; Fredric W. Scott, Brooktondale, all of N.Y.

[73] Assignee: Cornell Research Foundation, Inc., Ithaca, N.Y.

[21] Appl. No.: 12,691

[22] Filed: Feb. 16, 1979

[51] Int. Cl.$^2$ .................................................. A61K 39/12
[52] U.S. Cl. ............................................................. 424/89
[58] Field of Search ........................................... 424/89

[56] References Cited

U.S. PATENT DOCUMENTS

| | | | |
|---|---|---|---|
| 2,136,131 | 11/1938 | Green | 424/89 |
| 2,271,818 | 2/1942 | Green | 424/89 |
| 2,271,819 | 2/1942 | Green | 424/89 |
| 3,285,817 | 11/1966 | Slater | 424/89 |
| 3,293,130 | 12/1966 | Slater et al. | 424/89 |
| 3,346,456 | 10/1967 | Baker | 424/89 |
| 3,465,077 | 2/1969 | Baker | 424/89 |
| 3,520,972 | 7/1970 | Smith et al. | 424/89 |
| 3,562,387 | 2/1971 | Laverman | 424/89 |
| 3,577,525 | 5/1971 | Baker | 424/89 |

OTHER PUBLICATIONS

Binn, L. N. et al., Infection and Immunity 1(5):503–508, "Recovery and Characterization of a Minute Virus of Canines" (1970).

Siegl, G., "The Parvoviruses" in Virology Monographs #15, Springer–Verlag Wien, N.Y., p. 71 (1976).

Eugster, A. K. et al., Southwestern Veterinarian 30(1):59–60 (1977), "Diarrhea in Puppies: Parvovirus--Like Particles Demonstrated in Their Feces".

*Primary Examiner*—Shep K. Rose
*Attorney, Agent, or Firm*—Jones, Tullar & Cooper

[57] ABSTRACT

A vaccine against disease caused by canine parvoviruses (CPV) is produced using a modified live (attenuated) or chemically inactivated feline panleukopenia virus vaccine.

2 Claims, No Drawings

HETEROTYPIC CANINE PARVOVIRUS VACCINE

BACKGROUND OF THE INVENTION

The present invention relates to the method of protecting dogs against disease caused by canine parvovirus (CPV). More particularly, it relates to a method of immunizing dogs against CPV by using an alien infectious material from one animal species for the protection against natural disease in a different animal species. The vaccine that is the subject of this invention is a modified live (attenuated) or chemically inactivated feline panleukopenia virus vaccine.

Parvoviruses are characterized as a small animal DNA virus, consisting of an isometric protein capsid and a short molecule of single-stranded DNA. Until recently, there had been no definite isolation and laboratory propagation of a canine parvovirus, although parvoviruses have been recovered and isolated from various animal species (Siegl, *The Parvoviruses*, Springer-Verlag, New York, 1976). Bachmann et al. include the dog as a possible parvovirus host in a report detailing the characteristics of parvovirus in general (Bachmann et al., *Intervirology* 10: in press, 1978). In 1970, Binn et al. reported the recovery and characterization of a "minute virus of canines" (MVC) (Binn et al., *Infect. Immunity* 1: 503, 1970). The isolates described were of canine origin, however, their pathogenicity was not known, and cytopathic effect (CPE) was produced in only a very narrow host range, i.e., only in a single continuous canine cell line, and not in primary canine nor primary or continuous cell cultures from other species. No immunological testing was done. Present data suggest that the Binn isolate is distinct from the pathogenic canine parovirus which is the subject of this application. In 1977, Eugster and Nairn reported a circumstantially-suggested causative link between diarrhea in puppies and a canine parvovirus (Eugster and Nairn, *Southwestern Veterinarian* 30: 59, 1977). Consistent with Binn et al., above, the isolate reported therein could not be grown in more than a single cell line. Again, pathogenic potential was unexamined and no animal inoculations were performed. In 1978, an apparently new serious enteric disease in canines appeared and became widespread. It is characterized by diarrhea, fever, and diminished white blood cell counts.

The object of this invention is to provide a heterotypic feline viral vaccine for the protection of dogs against disease caused by pathogenic canine parvoviruses. While attempting to develop a homotypic vaccine against canine parvoviruses it was discovered that both living and inactivated commercial feline vaccines, when administered to dogs, provided protection against disease caused by CPV. The cross-relation between the feline panleukopenia virus (FPV) and the canine parvovirus (CPV) is a surprising result since such cross-relations are unusual among the various parvoviruses from different animal host species, e.g., swine-canine, bovine-swine, swine-feline, etc. (Siegl, G., "The Parvoviruses," *Virology Monographs* 15: Springer-Verlag, New York, 1976). The discovery of this immunological cross-relation represents a distinct advance in the art.

One group of dogs was vaccinated with a commercial modified living (attenuated) feline panleukopenia viral (FPLV) vaccine (Vacc. A); a second group was inoculated with a commercially available chemically inactivated feline panleukopenia viral vaccine (Vacc. C); and a third group with inactivated FPLV vaccine prepared in our laboratory by growing living attenuated FPLV (Leopard strain) (Vacc. L) in $CCL_{64}$ cells and by inactivating the virus with 0.25% formalin. According to the manufacturer, both commercial feline viral vaccines were produced by growing the FPV in cell cultures (tissue culture origin). The tissue cultures used for inactivated vaccine were treated with formaldehyde solution to insure viral inactivation. The vaccines were administered intramuscularly to dogs in doses of 1 cc. Neither the living nor inactivated FPLV vaccines caused any adverse effects in dogs during a 2-week period of observation prior to challenge-inoculation with virulent canine parvovirus. The vaccinated dogs in groups 1 and 2 and unvaccinated control dogs were challenge-inoculated 14 days after administration of one dose of FPLV living or inactivated vaccine. Dogs in group 3 were vaccinated twice, two weeks apart, and challenge-inoculated seven days after the last vaccination.

EXAMPLES

The results of vaccination with live feline panleukopenia vaccine are shown in Tables 1 and 2.

Table 1

Protective Immune Response of Dogs Inoculated with Living Heterotypic (FPLV) Vaccine* following Challenge with Virulent Canine Parvovirus (CPV). (Group 1)

| | | Antibody Titer (HA-HI) | | | | | |
|---|---|---|---|---|---|---|---|
| | | | | | Days Post-Virulent Virus Challenge | | |
| Dog | Status | Pre-Vaccination | 7 Days Post-Vaccination | 0 | 5 | 7 | Response to Challenge |
| A78-26/1 | Vacc. | Neg.⊕ | ≦80 | 320 | 800 | 800 | I** |
| /2 | Vacc. | Neg. | 1,280 | 320 | 800 | 12,800 | I |
| /3 | Vacc. | Neg. | 640 | 160 | 1,600 | 800 | I |
| /4 | Vacc. | Neg. | 320 | 1,600 | 800 | 800 | I |
| /9 | Vacc. | Neg. | 2,560 | 400 | 800 | 800 | I |
| /10 | Control | Neg. | Neg. | Neg. | 1,600 | 800 | S |
| /11 | Vacc. | Neg. | 400 | 160 | 6,400 | 6,400 | I |
| /12 | Vacc. | Neg. | 1,280 | 400 | 3,200 | 3,200 | I |
| /13 | Control | Neg. | Neg. | Neg. | 3,200 | 3,200 | S |

*Commercial attenuated feline panleukopenia vaccine 1 dose i.m. each 10-6-78 challenged i.v. as A78-25 series ($10^4$ $TCD_{50}$) 10-20-78
Nonvaccinated controls challenged as A78-25 series 10-20-78
⊕H-I antibody titers negative at lowest dilution of serum tested (1:80)
I = Immune; = Susceptible: characterized by fever, leukopenia, relative lymphopenia or other signs.

Table 2

Leukocyte Response of Dogs Before and After Challenge with Virulent Canine Parvovirus (CPV) following Attenuated Living Heterotypic (FPLV) Vaccine (Group 1)

Peripheral Blood WBC and Lymphocyte (L) Counts

| Dog No. | Status | Pre-CPV Challenge WBC* | L** | Post-Challenge Days 3 WBC | L | 4 WBC | L | 5 WBC | L | 7 WBC | L |
|---|---|---|---|---|---|---|---|---|---|---|---|
| A78-26/1 | Vacc. A.+ | 8.4 | 2.8 | 9.7 | 2.4 | 14.3 | 4.1 | 15.1 | 6.0 | 11.3 | 3.8 |
| 26/2 | Vacc. A. | 6.0 | 3.5 | 6.6 | 2.8 | 11.8 | 4.5 | 9.8 | 3.5 | 8.6 | 2.5 |
| 26/3 | Vacc. A. | 17.5 | 4.9 | 14.0 | 4.8 | 16.3 | 5.4 | 20.1 | 7.6 | 13.7 | 4.4 |
| 26/4 | Vacc. A. | 12.1 | 3.9 | 7.9 | 2.4 | 13.8 | 4.3 | 12.2 | 4.1 | 8.8 | 2.1 |
| 26/9 | Vacc. A. | 12.6 | 4.3 | 6.5 | 3.3 | 10.1 | 4.0 | 10.1 | 3.1 | 9.8 | 4.5 |
| 26/11 | Vacc. A. | 11.0 | 4.6 | 10.3 | 4.8 | 11.3 | 4.9 | 13.2 | 4.5 | 10.7 | 4.5 |
| 26/12 | Vacc. A. | 14.0 | 4.1 | 13.4 | 6.8 | 15.6 | 6.9 | 15.6 | 5.3 | 14.7 | 7.1 |
| A78-26/10 | Control++ | 10.6 | 4.3 | 15.6 | 1.0 | 10.7 | 1.3 | 5.4 | 1.6 | 6.1 | 2.4 |
| 26/13 | Control | 13.7 | 4.0 | 15.1 | 1.2 | 12.7 | 2.9 | 13.7 | 2.7 | 14.2 | 3.9 |

*Numbers indicate total white blood cell (WBC) count × 10³.
**Numbers indicate total lymphocyte count (L) × 10³.
+ Vacc. A. indicates those dogs vaccinated with attenuated, living FPLV vaccine.
++ In addition to relative lymphopenia one or more days following challenge inoculation, control dogs had temperatures in excess of 103.0° one or more post-challenge days. Vaccinated dogs remained normal.

The responses of dogs vaccinated with inactivated feline panleukopenia vaccine before and after challenge with virulent CPV are shown in Tables 3 and 4.

Table 3

Protective Immune Response of Dogs Inoculated with Inactivated Heterotypic (FPLV) Vaccine following Challenge with Virulent Canine Parvovirus (CPV)

| | Dog No. | Status | Antibody Titer (HA-HI) Pre-Vaccination | Pre-Challenge | 7 Days Post-Challenge | Response to Challenge** |
|---|---|---|---|---|---|---|
| Group 2 | A78-33/2 | Vacc. C.+ | Neg.* | 160 | 2,560 | I |
| | 33/5 | Vacc. C. | Neg. | 80 | 5,120 | I |
| Group 3 | A78-42/1 | Vacc. L.++ | Neg. | 1,280 | 640 | I |
| | 42/2 | Vacc. L. | Neg. | 160 | 640 | I |
| | 42/3 | Vacc. L. | Neg. | 320 | 640 | I |
| | 42/4 | Vacc. L. | Neg. | 320 | 320 | I |
| | A78-33/1 | Control+++ | Neg. | Neg. | 2,560 | S |
| | 33/6 | Control | Neg. | Neg. | 10,240 | S |
| | 42/5 | Control | Neg. | Neg. | 10,240 | S |
| | A79-2/1 | Control | Neg. | Neg. | 10,240 | S |

*Neg. indicated H-I titer less than 20.
**I = Immune; S = Susceptible: illness characterized by fever, leukopenia, relative lymphopenia or other signs.
+ Vacc. C. indicates dogs given a single 1 ml injection of inactivated FPLV vaccine (CU₄ strain).
++ Vacc. L. indicates dogs given two 1 ml injections two weeks apart, of inactivated FPLV vaccine (Leopard strain).
+++ In addition to relative lymphopenia one or more days following challenge inoculation, control dogs had temperatures in excess of 103.0° one or more post-challenge days. Vaccinated dogs remained normal.

tected, i.e., their resistance to virulent CPV was markedly enhanced. Protection was measured by the failure of vaccinated dogs to develop signs of disease (fever or

Table 4

Leukocyte Response of Dogs Before and After Challenge with Virulent Canine Parvovirus (CPV) Following Inactivated Heterotypic (FPLV) Vaccine Peripheral Blood WBC and Lymphocyte (L) Counts

| | Dog No. | Status | Pre-CPV Challenge WBC* | L** | 3 WBC | L | 4 WBC | L | 5 WBC | L | 6 WBC | L |
|---|---|---|---|---|---|---|---|---|---|---|---|---|
| Group 2 | A78-33/2 | Vacc. C+ | 8.8 | 4.1 | 10.2 | 2.7 | 9.1 | 2.1 | 10.8 | 3.3 | 9.0 | 4.5 |
| | 33/5 | Vacc. C. | 16.3 | 8.5 | 13.9 | 6.3 | 1.3 | 3.4 | 13.1 | 5.0 | 12.1 | 5.4 |
| Group 3 | A78-42/1 | Vacc. L.++ | 10.6 | 4.8 | 16.9 | 5.8 | 14.4 | 4.1 | 19.8 | 7.4 | 15.4 | 5.4 |
| | 42/2 | Vacc. L. | 12.5 | 4.2 | 16.3 | 5.7 | 13.5 | 5.1 | 15.9 | 5.8 | 22.1 | 9.2 |
| | 42/3 | Vacc. L. | 13.6 | 4.9 | 14.0 | 6.0 | 15.1 | 6.4 | 10.6 | 4.3 | 13.4 | 5.2 |
| | 42/4 | Vacc. L. | 14.4 | 3.8 | 1.7 | 3.1 | 13.5 | 4.4 | 13.6 | 4.7 | 17.1 | 6.3 |
| | A78-33/1 | Control+++ | 14.3 | 6.2 | 17.1 | 1.1 | 10.3 | 3.3 | 17.2 | 4.0 | 14.2 | 4.0 |
| | 33/6 | Control | 15.9 | 4.9 | 20.2 | 0.8 | 24.4 | 2.4 | 19.2 | 3.6 | 9.1 | 3.0 |
| | 42/5 | Control | 13.3 | 5.8 | 14.2 | 4.0 | 25.5 | 1.0 | 23.8 | 5.9 | 15.8 | 4.8 |
| | A79-2/1 | Control | 12.2 | 4.5 | 14.2 | 1.1 | 19.7 | 1.9 | 12.3 | 1.7 | 13.6 | 5.2 |

*Numbers indicate total white blood cell (WBC) count × 10³.
**Numbers indicate total lymphocyte count (L) × 10³.
+ Vacc. C. indicates dogs given a single 1 ml injection of inactivated FPLV vaccine (CU₄ strain).
++ Vacc. L. indicates dogs given two 1 ml injections two weeks apart, of inactivated FPLV vaccine (Leopard strain).
+++ In addition to relative lymphopenia one or more days following challenge inoculation, control dogs had temperatures in excess of 103.0° one or more post-challenge days. Vaccinated dogs remained normal.

All dogs vaccinated with the attenuated living or inactivated feline panleukopenia vaccines were prorelative lymphopenia), and, prior to challenge with virulent canine parvovirus, the development of canine parvovirus hemagglutinin-inhibiting antibody response. The unvaccinated control dogs were all susceptible.

Hemagglutination (HA)/Hemagglutination Inhibition (HI) tests for CPV.

Hemagglutination tests were performed at 2° C.–4° C. with 1% pig erythrocytes (PRC) at pH 7.4. The highest dilution of antigen in 0.05 ml giving 2+ HA was the endpoint. For the HA-HI tests the sera specimens were treated with a receptor-destroying enzyme (RDE) (Microbiological Associates, Cat. #30899). If isoagglutinins in the canine test serum for PRC were greater than 1:20, the serum was absorbed with 0.1 ml of 50% packed swine erythrocytes. Serum dilutions were started at 1:20 and two-fold dilutions were made using 0.025 ml diluters. 0.025 ml of antigen diluted to contain 4–8 units of HA was added and the mixtures were incubated for one hour at room temperature. The PRC suspension (0.05 ml) was added, mixed, and the test was incubated at 2° C.–4° C. for 2–4 hours. The highest dilution of serum that inhibited HA by 4–8 units of CPV antigen was the endpoint. The hemagglutination-inhibition titer was expressed as the reciprocal of the highest endpoint serum dilution (Tables 1 and 3).

The peripheral white blood cell and lymphocyte counts of both vaccinated and control groups are shown in Tables 2 and 4.

We claim:

1. The method of protecting dogs against disease caused by virulent canine parvovirus which comprises inoculating the animal with a modified live feline panleukopenia virus vaccine.

2. The method of protecting dogs against disease caused by virulent canine parvovirus which comprises inoculating a dog with chemically inactivated feline panleukopenia vaccine.

* * * * *